United States Patent [19]

Sandweiss et al.

[11] Patent Number: 4,489,070
[45] Date of Patent: * Dec. 18, 1984

[54] BETAMETHASONE DIPROPIONATE CREAM

[75] Inventors: Varda E. Sandweiss, Forest Hills, N.Y.; Elliot Stupak; Paul H. Shapiro, both of West Caldwell, N.J.

[73] Assignee: Schering Corporation, Madison, N.J.

[*] Notice: The portion of the term of this patent subsequent to Nov. 13, 2001 has been disclaimed.

[21] Appl. No.: 550,434

[22] Filed: Nov. 10, 1983

Related U.S. Application Data

[63] Continuation-in-part of Ser. No. 494,214, May 13, 1983.

[51] Int. Cl.³ .............................................. A61K 31/56
[52] U.S. Cl. ...................................................... 424/243
[58] Field of Search ......................................... 424/243

[56] References Cited

U.S. PATENT DOCUMENTS

| | | | |
|---|---|---|---|
| 3,312,590 | 4/1967 | Elks et al. | 424/243 |
| 3,934,013 | 1/1976 | Poulsen | 424/239 |
| 4,370,322 | 1/1983 | Busset et al. | 424/243 |
| 4,404,200 | 9/1983 | Thalen et al. | 260/239.55 D |

*Primary Examiner*—Elbert L. Roberts
*Attorney, Agent, or Firm*—Stephen I. Miller; Bruce M. Eisen; Warrick E. Lee, Jr.

[57] ABSTRACT

Disclosed is an elegant formulation of betamethasone dipropionate useful as a topical anti-inflammatory product.

4 Claims, No Drawings

BETAMETHASONE DIPROPIONATE CREAM

This is a continuation-in-part of U.S. application Ser. No. 494,214, filed May 13, 1983.

This invention relates to an elegant formulation of betamethasone dipropionate.

A betamethasone dipropionate cream has been sold by Schering Corporation under the trademark Diprosone. That product consists of betamethasone dipropionate in a cream consisting of purified water, mineral oil, white petrolatum, polyethylene glycol 1000 monocetyl ether, cetostearyl alcohol, monobasic sodium phosphate and phosphoric acid, with 4-chloro-m-cresol and propylene glycol as preservatives.

The formulation of the present invention is remarkably simple compared to Diprosone cream. It contains a glycol solvent as a major component, but it is free of any other preservative and contains no surfactants. It is thus less likely to cause allergic reactions due to these additives. Nevertheless, the formulation of the present invention is highly efficacous and is stable. In fact, it is surprisingly more effective than Diprosone cream. Also, even though standard preservatives are not present, the present formulation has been found to be self preserving when tested in standardized assays for the determination of growth of *Eschericia coli, Candida albicans, Staphylococcus aureus, Aspergillis niger,* and *Pseudomonas aeruginosa*. In standard dermal irriration studies on rabbits, the formulation of the present invention has been found to be less irritating than Diprosone cream.

The formulation of this invention is of value in the topical treatment of dermatological disorders that are responsive to corticosteroids. Included within this category are disorders such as psoriasis, contact dermatitis, atopic dermatitis and eczema. Treatment with the formulation of this invention is usually accomplished by applying it to completely cover the affected area. The usual frequency of application is twice daily, although adequate maintenance therapy for some patients may be achieved with less frequent application.

The formulation of the present invention consists essentially of about 0.02 to 0.10 percent betamethasone dipropionate, about 0 to 0.6 percent titanium dioxide, about 1.0 to 2.5 percent Carbomer 940, sufficient base to maintain the pH to between pH 4.0 and pH 5.5, and about 60 to 80 percent of propylene glycol and about 20 to 40 percent water (all percentages are by weight).

In a preferred aspect of the present invention, 0.06 to 0.08 betamethasone dipropionate is employed; 65 to 75 percent of propylene glycol and 25 to 35 percent water. The preferred based is sodium hydroxide.

Carbomer 940 is an acrylic acid polymer having an approximate molecular weight of 4,000,000. It is available from B. F. Goodrich Chemical Company of as Carbopol 940 resin.

This formulation results in an elegant cream-like gel when it contains from 0.4 to 0.6 titanium dioxide. If no titanium dioxide is used, a clear gel-like consistency is attained. The formulations are surprisingly more effective than the Diprosone cream known in the art.

The formulations of the present invention are manufactured in a conventional manner by thoroughly mixing the ingredients at ambient or elevated temperatures. Preferably, the betamethasone dipropionate, dissolved in a portion of propylene glycol, is added to the cream-like gel. The ingredients are thoroughly mixed so that the product is homogenous. If desired, additional mechanical agitation can be used as an intermediate or final step in the manufacturing process to impart more homogeneity or improve texture. Processing equipment suitable for these steps is known and includes that exchangers, propeller mixers, colloid mills, homogenizers, roller mills and the like.

The following formulation examples illustrate the compositions of the present invention. It will be apparent to those skilled in the art that many modifications thereof may be practiced without departing from the purpose and intent of this disclosure.

EXAMPLE 1

| Betamethasone Dipropionate Cream | | | |
|---|---|---|---|
| | Formulation (mg/g) | | |
| Ingredients | I | II | III |
| Betamethasone 17,21-dipropionate USP | 0.7 | 0.7 | 1.0 |
| Titanium Dioxide USP | 5.0 | 5.0 | 5.0 |
| Carbomer 940 | 20.0 | 15.0 | 15.0 |
| Sodium Hydroxide USP | 0.4 | 0.3 | 0.3 |
| Propylene Glycol USP | 700.0 | 700.0 | 800.0 |
| Purified Water USP | 273.9 | 279.0 | 178.7 |

What is claimed is:

1. A topical pharmaceutical composition for the treatment of inflammation consisting essentially of 0.02 to 0.10 percent betamethasone dipropionate; 0 to 0.6 percent titanium dioxide; 1.0 to 2.5 percent Carbomer 940; sufficient base to adjust the pH to between pH 4 to pH 5.5; and about 60 to 80 percent of propylene glycol and about 20 to 40 percent water.

2. A pharmaceutical composition according to claim 1 wherein Carbomer 940 is present in an amount of about 2% by weight.

3. A pharmaceutical composition according to claim 1 consisting essentially of 0.06 to 0.08 percent betamethasone dipropionate; about 1.0 to 2.5 percent Carbomer 940; sufficient base to adjust the pH to between pH 4 to pH 5.5; and about 65 to 75 percent of propylene glycol and about 25 to 35 percent water.

4. A pharmaceutical composition according to claim 1 wherein said base is sodium hydroxide.

* * * * *